US00PP34948P3

(12) United States Plant Patent
Meir

(10) Patent No.: US PP34,948 P3
(45) Date of Patent: Jan. 31, 2023

(54) ***VACCINIUM* PLANT NAMED 'VACBRI2'**

(50) Latin Name: *Vaccinium ovatum*
Varietal Denomination: Vacbri2

(71) Applicant: Gurjit Sidhu, Mission (CA)

(72) Inventor: Corey Meir, Centralia, WA (US)

(73) Assignee: Gurjit Sidhu, Mission (CA)

( * ) Notice: Subject to any disclaimer, the term of this patent is extended or adjusted under 35 U.S.C. 154(b) by 0 days.

(21) Appl. No.: 17/710,008

(22) Filed: Mar. 31, 2022

(65) Prior Publication Data

US 2022/0338397 P1 Oct. 20, 2022

(30) Foreign Application Priority Data

Apr. 15, 2021 (CA) ..... CA 21-10459

(51) Int. Cl.
*A01H 5/08* (2018.01)
*A01H 6/36* (2018.01)

(52) U.S. Cl.
USPC ..... Plt./156
CPC ..... *A01H 6/368* (2018.05)

(58) Field of Classification Search
USPC ..... Plt./156, 157
CPC ..... A01H 5/08; A01H 5/00
See application file for complete search history.

*Primary Examiner* — Kent L Bell
(74) *Attorney, Agent, or Firm* — Penny J. Aguirre

(57) ABSTRACT

A new cultivar of *Vaccinium* plant named 'Vacbri2' that is characterized by its young foliage that emerges pink in color and its maturing and mature foliage that is variegated with creamy white speckles.

2 Drawing Sheets

Botanical classification: *Vaccinium ovatum.*
Cultivar designation: 'Vacbri2'.

CROSS REFERENCE TO RELATED APPLICATIONS

This application claims priority to a Canadian Plant Breeder's Rights Application No. 21-10459 filed on Apr. 15, 2021, under 35 U.S.C. 119(f), the entire contents of which is incorporated by reference herein. This application is also related to U.S. Plant Patent for a plant derived from the same breeding program that is entitled *Vaccinium* Plant Named 'Vacsid1' (U.S. Plant Pat. No. 25,067).

BACKGROUND OF THE INVENTION

The present invention relates to a new and distinct cultivar of *Vaccinium ovatum*, and will be referred to hereafter by its cultivar name, 'Vacbri2'. 'Vacbri2' is a new cultivar of huckleberry grown for use as a landscape shrub.

The new cultivar was discovered by the Inventor in spring of 2017 as a naturally occurring branch mutation of an unnamed and unpatented plant of *Vaccinium ovatum* that was growing in a container at a nursery in Elma, Wash.

Asexual propagation of the new cultivar was first accomplished under the direction of the Inventor by tissue culture using meristematic tissue in Elma, Wash. in spring of 2018. Asexual propagation by tissue culture has determined that the characteristics of this cultivar are stable and are reproduced true to type in successive generations.

SUMMARY OF THE INVENTION

The following traits have been repeatedly observed and represent the characteristics of the new cultivar, which in combination distinguish 'Vacbri2' as a new and distinct cultivar of *Vaccinium.*

1. 'Vacbri2' exhibits young foliage that emerges pink in color.
2. 'Vacbri2' exhibits maturing and mature foliage that is variegated with creamy white speckles.

The parent plant of 'Vacbri2' differs from 'Vacbri2' in having foliage that is green in color and not variegated with speckles. 'Vacbri2' can also be compared to the *Vaccinium ovatum* cultivar 'Vacsid1' (U.S. Plant Pat. No. 25,067). 'Vacsid1' is similar to 'Vacbri2' in having brightly colored new growth. 'Vacsid1' differs from 'Vacbri2' in having foliage with reddish colored new growth, solid green (non-speckled) maturing and mature foliage, and in having a more dwarf plant habit.

STATEMENT REGARDING PRIOR DISCLOSURES BY THE INVENTOR

The Applicant asserts that no publications or advertisements relating to sales, offers for sale, or public distribution occurred more than one year prior to the effective filing date of this application. Any information about the claimed plant would have been obtained from a direct or indirect disclosure from the Inventor. The Applicant claims a prior art exemption under 35 U.S.C. 102(b)(1) for disclosure and/or sales prior to the filing date but less than one year prior to the effective filing date. Disclosures include but may not be limited to website listings by Nursery Guide, Briggs Nursery, National Nursery & Greenhouse Trade Show, Hortibiz, Farwest Show, Raintree Nursery, One Green World, Bremerton City Nursery, Pheonix Perennials and Specialty Plants, Lawn and Garden Retailer, Green House Grower, and Venternet, and Hortweek.

BRIEF DESCRIPTION OF THE DRAWINGS

The accompanying color photographs illustrate the overall appearance and distinct characteristics of the new *Vac-*

*cinium*. The photographs were taken of 2 year-old plants of the new cultivar as grown in a greenhouse in Elma, Wash.

Figure 1:
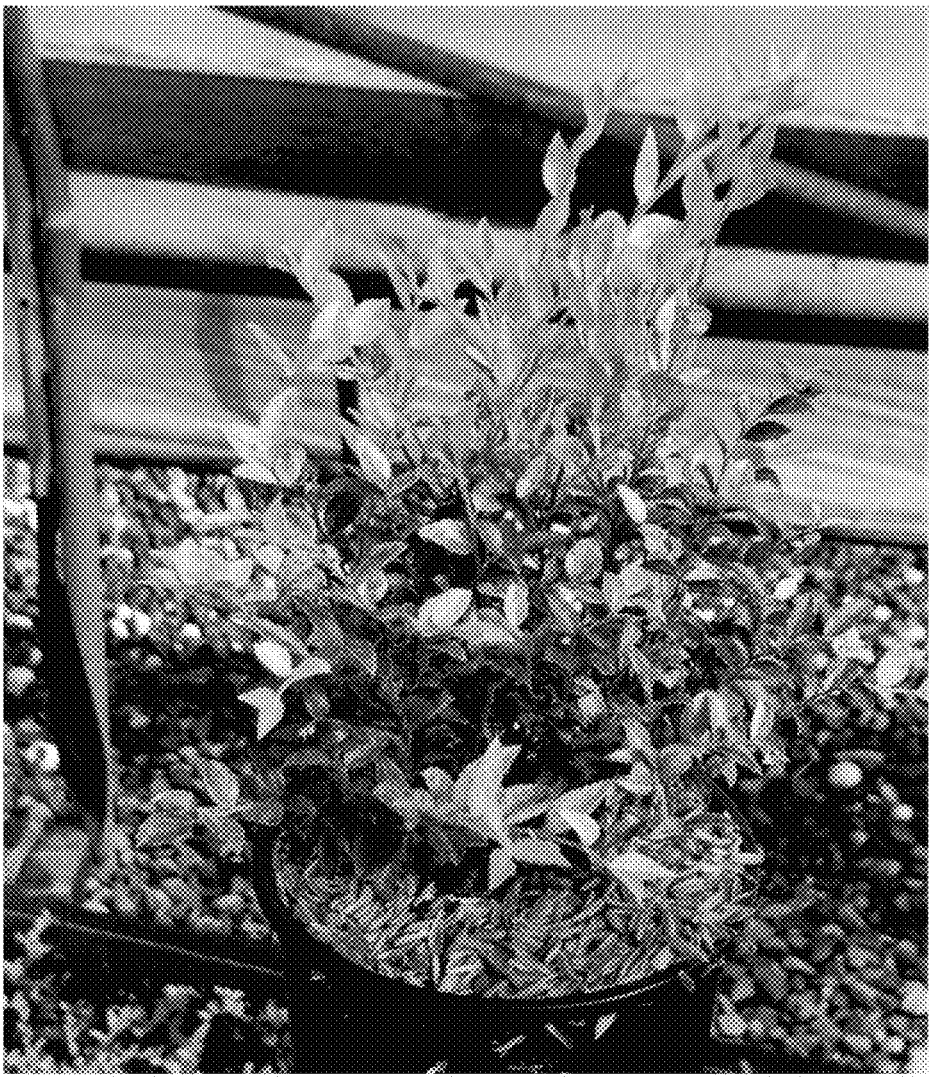

The photograph in FIG. 1 provides a view of the foliage of 'Vacbri2'.

Figure 2:
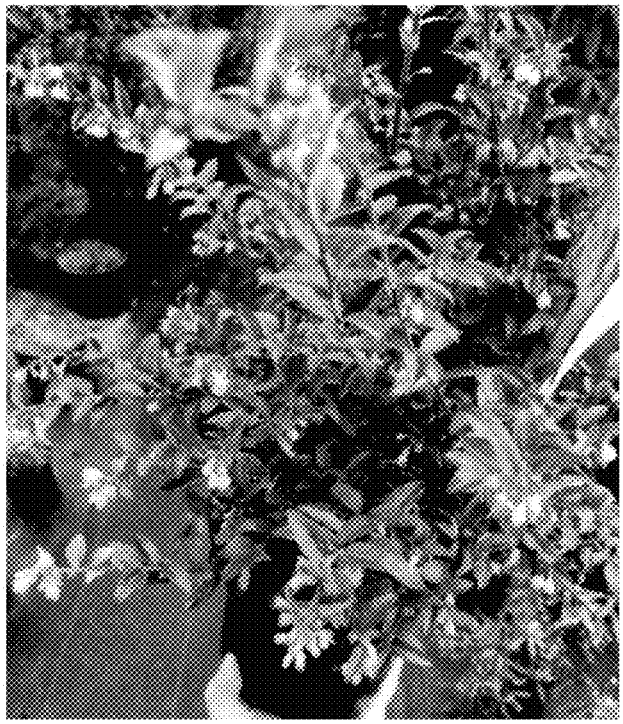

The photograph in FIG. 2 provides a view of 'Vacbri2' in bloom.

Figure 3:
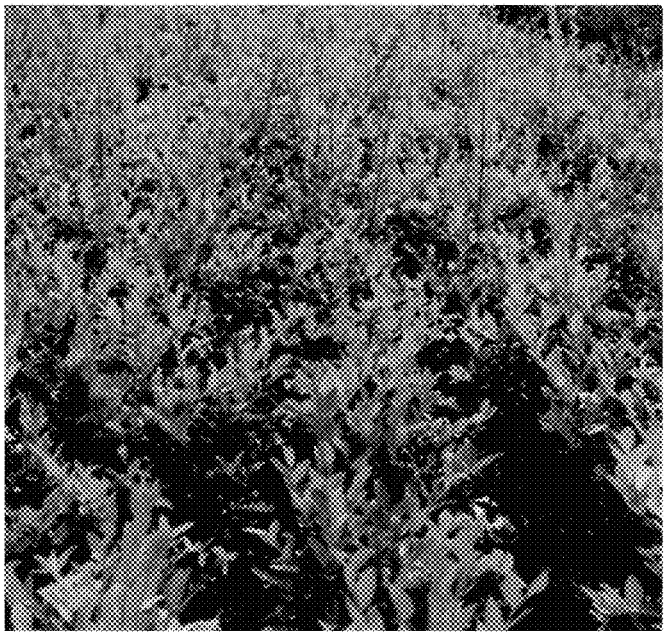

The photograph in FIG. 3 provides a view of a production block of 'Vacbri2'.

The colors in the photographs are as close as possible with the digital photography and printing techniques utilized and the color codes in the detailed botanical description accurately describe the new *Vaccinium*.

DETAILED BOTANICAL DESCRIPTION OF THE PLANT

The following is a detailed description of 2-year-old plants of the new cultivar as grown outdoors in 1-gallon containers in Elma, Wash. The phenotype of the new cultivar may vary with variations in environmental, climatic, and cultural conditions, as it has not been tested under all possible environmental conditions. The color determination is in accordance with The 2007 Colour Chart of The Royal Horticultural Society, London, England, except where general color terms of ordinary dictionary significance are used.

General plant characteristics:

*Blooming period.*—Late spring in in Elma, Wash.

*Plant type.*—Evergreen shrub.

*Plant habit.*—Semi-erect.

*Height and spread.*—Average of 30 cm in height, 38.1 cm in width as a 2-year-old plant in a one-gallon container and 1.2 m in height and width as a mature plant in the landscape.

*Hardiness.*—Hardy in at least U.S.D.A. Zones 7 to 8.

*Disease and pest resistance.*—No susceptibility or resistance to diseases or pests has been observed.

*Root description.*—Fibrous.

*Growth rate.*—Moderate.

*Propagation.*—Tissue culture.

*Root development.*—A tissue culture plantlet will root in a small plug in 3 months and a transplanted rooted plug will finish in a liner in 5 to 6 months.

Stem description:

*Stem shape.*—Rounded.

*Stem color.*—Young; 47B to 47C and occasionally 144A and 161A, mature; 181B, old stems and bark; 165A, fissures 165B.

*Branching.*—Medium to strongly branched, an average of 1 main branch and 10 lateral stems.

*Stem surface.*—Older stems matte, younger stems moderately glossy, all stems moderately to densely covered with pubescent hairs, an average of 1 mm in length and 161C in color.

*Stem size.*—An average of 31.8 cm in length, 2.6 mm in width.

*Stem strength.*—Medium to strong.

*Internodes.*—2.5 cm in length.

Foliage description:

*Leaf shape.*—Ovate.

*Leaf division.*—Simple.

*Leaf base.*—Rounded.

*Leaf apex.*—Acute.

*Leaf venation.*—Pinnate, color on upper and lower surfaces matches leaf coloration.

*Leaf margins.*—Entire.

*Leaf attachment.*—Petiolate.

*Leaf arrangement.*—Alternate.

*Leaf orientation.*—Held slightly upward.

*Leaf surface.*—Both surfaces moderately glossy, sparsely pubescent.

*Leaf color.*—Newly expanded leaves upper surface; spring 52B to 52C, summer 35A to 35B, newly expanded leaves lower surface; spring 52A, summer 37B, mature leaves upper surface; 147A, mature leaves lower surface; 147C, young variegated leaves upper surface; 144A mottled with N144A, 150B, and 8B, young variegated leaves lower surface; 191A mottled with 144B, 145D and 6D, mature variegated leaves upper surface; NN137A mottled with closest to 144B to 144C and 4C, mature variegated leaves lower surface; 138C mottled with 145C and 145D.

*Leaf size.*—Average of 2.3 cm in length, 1.3 cm in width.

*Petioles.*—Round in shape, an average of 2.3 mm in length and 1.2 mm in width, 145B in color, glabrous surface.

*Stipules.*—None observed.

Inflorescence description:

*Bloom season.*—Buds burst mid-April in Elma, Wash., flowering begins in May in Elma, Wash. as grown in a greenhouse, bud burst and bloom time are highly variable depending on season.

*Inflorescence type.*—Cluster.

*Inflorescence size.*—Average of 3.1 cm in length 3.0 cm in width.

*Lastingness of inflorescence.*—Average of 28 days but highly dependent on air temperatures.

*Number of flowers.*—Average of 10 per inflorescence, range of 6 to 12.

*Flower fragrance.*—None to slight.

*Flower size.*—Average of 8.2 mm in length and 6.3 mm in width.

*Flower buds.*—10 per inflorescence, ovate in shape, 6 mm in length and 4 mm in width, 46D in color.

*Corolla.*—Urceolate in shape, comprised of 5 fused petals with tip free and curled under, average of 8.2 mm in length and 6.3 mm in width, aperture is an average of 3.4 mm in diameter, color NN155A on outer and inner surface with outer surface sometimes tinged with 51A with sun exposure, glabrous texture on both surfaces.

*Calyx.*—Campanulate, comprised of 5 fused sepals with lobes free at apex, average of 8 mm in diameter, free sepal lobes an average of about 3 mm in length and 3.5 mm in width at anthesis, color 144A to 144B on outer and inner surface and tinged at the distil end with 51A with sun exposure, surface glabrous, entire margins.

*Pedicels.*—Round, average of 5.5 mm in length and 1.1 mm in width, closest to 143D in color and slightly suffused with 51A, surface is glabrous.

*Peduncles.*—Round, an average of 7 mm in length and 1.6 mm in width, closest to 144C in color, surface is glabrous.

Reproductive organs:

*Androecium.*—10 stamens, stamens are 6 mm in length, anthers are 9A in color and 1 mm in length, filaments are 5 mm in length and 145C in color, pollen is moderate in abundance and 9A in color.

*Gynoecium.*—1 pistil, style is cone-shaped, an average of 8 mm in length (approximately equal to tip of corolla) and 145B in color, ovary 144A in color.

Fruit description:

*Type.*—Berry.

*Number.*—4 to 10 per cluster.

*Cluster tightness.*—Medium.

*Skin color.*—Immature 138B, maturing a blend of 93A and 103A.

*Fruit use.*—Not grown for fruit production.

*Fruit bearing season.*—Mid to late summer in Elma, Wash.

*Fruit size.*—Medium to large, an average of 4 mm in diameter and height.

*Fruit shape.*—Globose.

*Persistence of calyx.*—Not persistent.

*Fruit surface.*—Glossy, smooth, glabrous.

*Color of flesh.*—194A to 194C.

*Seeds.*—Oblong to oval in shape, numerous, less than 1 mm in length and width, 171B in color.

It is claimed:

1. A new and distinct cultivar of *Vaccinium* plant named 'Vacbri2' as herein illustrated and described.

* * * * *